US012582587B2

(12) United States Patent
Stahl et al.

(10) Patent No.: US 12,582,587 B2
(45) **Date of Patent: *Mar. 24, 2026**

(54) SUNSCREEN COMPOSITION AND METHODS OF PROTECTION FROM ULTRAVIOLET AND VISIBLE LIGHT

(71) Applicant: DOC MARTIN'S OF MAUI, Kihei, HI (US)

(72) Inventors: Christopher Ryan Stahl, Pioneertown, CA (US); Curtis Allan Cole, New Holland, PA (US); George Michael Martin, Kula, HI (US)

(73) Assignee: DOC MARTIN'S OF MAUI, Kihei, HI (US)

(*) Notice: Subject to any disclaimer, the term of this patent is extended or adjusted under 35 U.S.C. 154(b) by 6 days.

This patent is subject to a terminal disclaimer.

(21) Appl. No.: 18/784,316

(22) Filed: Jul. 25, 2024

(65) Prior Publication Data

US 2024/0374490 A1 Nov. 14, 2024

Related U.S. Application Data

(63) Continuation of application No. 17/895,911, filed on Aug. 25, 2022, now Pat. No. 12,076,426.

(60) Provisional application No. 63/260,980, filed on Sep. 8, 2021.

(51) Int. Cl.
| | |
|---|---|
| *A61K 8/27* | (2006.01) |
| *A61K 8/29* | (2006.01) |
| *A61K 8/67* | (2006.01) |
| *A61Q 17/04* | (2006.01) |

(52) U.S. Cl.
CPC ................. *A61K 8/27* (2013.01); *A61K 8/29* (2013.01); *A61K 8/676* (2013.01); *A61K 8/678* (2013.01); *A61Q 17/04* (2013.01); *A61K 2800/43* (2013.01); *A61K 2800/522* (2013.01); *A61K 2800/623* (2013.01)

(58) Field of Classification Search
None
See application file for complete search history.

(56) References Cited

U.S. PATENT DOCUMENTS

| | | | |
|---|---|---|---|
| 5,939,054 | A | 8/1999 | Msika et al. |
| 5,976,510 | A | 11/1999 | Cernasov et al. |
| 6,159,481 | A | 12/2000 | Fallick |
| 10,278,905 | B1 | 5/2019 | Byren et al. |
| 2004/0116511 | A1 | 6/2004 | Malik |
| 2006/0165645 | A1 | 7/2006 | Lebok et al. |
| 2007/0280895 | A1 | 12/2007 | Weimer et al. |
| 2007/0286826 | A1 | 12/2007 | Grune |
| 2007/0298000 | A1 | 12/2007 | Grune |
| 2008/0219938 | A1 | 9/2008 | Grune |
| 2008/0233060 | A1 | 9/2008 | Grune |
| 2010/0061947 | A1 | 3/2010 | Schlossman et al. |
| 2011/0318286 | A1 | 12/2011 | Kawasaki et al. |
| 2018/0296455 | A1 | 10/2018 | Blachechen et al. |

FOREIGN PATENT DOCUMENTS

| | | |
|---|---|---|
| CN | 109077952 B | 8/2020 |
| EP | 1536754 B1 | 5/2015 |

OTHER PUBLICATIONS

Cole et al., "Metal oxide sunscreens protect skin by absorption, not by reflection or scattering," Photodermatol Photoimmunol Photomed, 2016, 32: 5-10.
Rodriquez, Kari (PCT Authorized Officer), International Search Report and Written Opinion issued Nov. 3, 2022 in corresponding International Application No. PCT/US2022/041591, 8 pages.
Extended European Search Report for European Application No. 22867904.9 dated Jul. 24, 2025, 13 pages.
Database GNPD (Online), Mintel, "BB Cream 5-in-1 'Baby Skin' Effect Makeup-Care Face Cream SPF 20," Database Accession No. 8567309, Mar. 19, 2021, Abstract (Product Description), XP093285072, 4 pages.

*Primary Examiner* — Nannette Holloman
(74) *Attorney, Agent, or Firm* — MH2 Technology Law Group LLP

(57) ABSTRACT

Provided herein is a method of reducing or preventing sunburn caused from visible and ultraviolet radiation in a subject, the method comprising topically applying to the subject a sunscreen composition comprising inorganic UV filtering agents, antioxidants, and at least one inorganic pigment, wherein the at least one inorganic pigments and antioxidants are present in an amount effective to reduce or prevent sunburn caused from visible light. Also provided herein are sunscreen compositions and methods of increasing the SPF of a sunscreen composition that comprises at least one inorganic UV filtering agent.

20 Claims, No Drawings

SUNSCREEN COMPOSITION AND METHODS OF PROTECTION FROM ULTRAVIOLET AND VISIBLE LIGHT

CROSS-REFERENCE TO RELATED APPLICATION

This application is a Continuation of U.S. application Ser. No. 17/895,911 filed 25 Aug. 2022 (Allowed), which claims the benefit of U.S. Provisional Application No. 63/260,980, filed 8 Sep. 2021, the disclosures of which are hereby incorporated herein by reference in their entireties.

DETAILED DESCRIPTION

Field of the Disclosure

Disclosed herein are compositions for topical sun protection comprising a combination of ultraviolet (UV) filtering agents, at least one inorganic pigment, and antioxidants, including vitamin E, vitamin C or derivatives thereof, such as tocopherol acetate and tetrahexadecyl ascorbate. The compositions disclosed herein may be used to protect against both visible light-induced erythema and ultraviolet radiation-induced erythema.

BACKGROUND

The electromagnetic spectrum is a spectrum comprising the range of frequencies of electromagnetic radiation and its associated wavelengths, spanning from the lowest wavelength radio waves to the highest wavelength gamma ionizing radiation waves. Beginning with the lowest frequency waves, the spectrum is divided into the following bands: radio waves, microwaves, infrared, visible light, ultraviolet, X-rays, and gamma rays. Initially, only visible light, which has corresponding wavelengths ranging from about 400 nm to about 700 nm, was known to exist. In 1801, however, the UV portion of the electromagnetic spectrum, having corresponding wavelengths ranging from about 10 nm to about 400 nm, was discovered by Johann Ritter to be photochemically and photobiologically active. The most common source of UV light is the sun, and it is the radiation originating from UV light that is responsible for what is commonly referred to as "sunburn" or "erythema." The UV band of the electromagnetic spectrum itself contains a subspectrum of three bands: UVA (about 320-400 nm), UVB (about 280-320 nm), and UVC (about 100-280 nm).

Sunburn is a reddening of the skin resulting from prolonged exposure to the sun. The severity of sunburn can range from mild to severe, based on several factors including the length of exposure, intensity of exposure, and an individual's skin type, with fair skin being at a greater risk. Sunburn is a well-recognized risk factor for skin cancer.

Until recently, it was thought that sunburn was caused exclusively by light in the UV wavelength range (i.e., from 10-400 nm), with no meaningful contribution to sunburn from visible light wavelengths (i.e., above 400 nm). The UV-induced erythema commonly known as sunburn was considered to be induced by direct absorption damage to specific chromophores (primarily DNA) and other proteins in the epidermis and dermis, cause by exposure to UVB radiation, as well as by indirect damage by photo-oxidative processes caused by UVB and UVA radiation. For UVA-induced photo-oxidative damage, the radiation energy absorbed causes oxygen to rise to a triplet or singlet excited energy level, making it capable of interacting with and damaging other surrounding cellular structures, and ultimately resulting in erythema of the skin when present in sufficient quantities.

Action spectra were derived to describe the precise amounts of radiation required to cause erythema at each specific wavelength and have been reported as covering the wavelength range from around 250-400 nm. All published action spectra for erythema stop precisely at 400 nm, with the implication being that wavelengths above 400 nm were of no consequence and had no contribution to the erythema reaction. See, e.g., Schmalwieser, A. et al., *A library of action spectra for erythema and pigmentation*, PHOTOCHEM. PHOTOBIOL. SCI. 2012; 11 (2):252-268.

Recently, it was discovered that this assumption is incorrect, and that the visible light portion of the electromagnetic spectrum, and particularly the violet and/or blue light region from about 400-500 nm, can and does have an impact on the induction of erythema, particularly when considering outdoor sun exposures where the sun produces copious amounts of visible light (e.g., 50%) compared with the relatively minor (e.g., 5%) amount of ultraviolet light at terrestrial levels. For example, Zastrow and colleagues demonstrated that free radicals (excited oxygen molecules) can be generated in skin tissue by wavelengths across the ultraviolet and the entire visible light spectrum. When combining the action spectrum with the terrestrial solar spectrum, it was estimated that as much as 50% of the free radicals generated by sunlight are caused by the visible portion of the sun's spectrum, and the other 50% from the ultraviolet portion. Zastrow, L. et al., *The missing link, light* (280-1600 nm) *induced free radical formation in human skin*, SKIN PHARMACOL. PHYSIOL. 2009; 22:31-34.

Nonetheless, the active ingredients in traditional sunscreen products typically aim only to filter UV rays (primarily UVA and UVB), and are not concerned with the effects of visible light. Typical UV absorbers in sunscreen products may be either organic (e.g., avobenzone, oxybenzone, octyl methoxycinnamate, etc.) or inorganic (i.e., titanium dioxide, zinc oxide, etc.). Manufacturers of these products have worked arduously to produce non-visible sunscreen products, as many consumers do not want to have the sunscreen visible on their skin. While zinc oxide and titanium dioxide are widely used for sunscreen products since around 1987, they are typically incorporated into sunscreen products using very small particles sizes, such as nanosized particles. Nanosized particles may minimize the visible appearance of the zinc oxide and titanium dioxide, making the sunscreen product virtually invisible on the skin after application, while still functioning to absorb the harmful effects of UV radiation from the sun. See Cole C. et al., *Metal oxide sunscreens protect skin by absorption, not by reflection or scattering*, PHOTOMED. PHOTOIMMUNOL. PHOTODERMATOL. 2016 32:1, 5-10.

The nano-particle sized zinc oxide and titanium dioxide may still function as UV filters, as they still operate as semi-conducted absorbers of UV radiation below about 370-380 nm, depending on their band-gap energy. Nonetheless, nano-particle sized zinc oxide and titanium dioxide largely do not scatter and reflect radiation above these wavelengths because of their micronized/nano-particle size. Thus, even these inorganic base sunscreens offer little to no protection against radiation in the visible light portion of the electromagnetic spectrum, and may offer diminished protection for wavelengths at the higher end of the UVA spectrum (e.g., 375-400 nm).

Therefore, there is a need for a sunscreen composition that provides protection against both the UV radiation in sunlight and also the visible light portion of the sun's spectrum. Ideally, such a sunscreen composition should be consumer-acceptable in appearance and provide greater protection to the skin against erythema than conventional UV-only protection sunscreen products.

SUMMARY

Disclosed herein are sunscreen compositions and methods of using sunscreen compositions to reduce or prevent sunburn caused from both visible light and ultraviolet (UV) radiation, as well as methods of increasing the sunscreen protection factor (SPF) of the sunscreen composition.

In certain embodiments, disclosed herein is a sunscreen composition comprising (a) inorganic UV filtering agents comprising or consisting of zinc oxide and titanium dioxide, present in the sunscreen composition in a total amount ranging from about 10% to about 50% by weight based on a total weight of the sunscreen composition; (b) antioxidants comprising or consisting of vitamin E or derivatives thereof and vitamin C or derivatives thereof, present in the sunscreen composition in a total amount ranging from about 0.1% to about 5% by weight relative to the total weight of the sunscreen composition; and (c) at least one inorganic pigment comprising or consisting of iron oxide present in the sunscreen composition in a total amount ranging from about 0.1% to about 10% by weight relative to the total weight of the sunscreen composition, wherein the at least one inorganic pigment and the antioxidants are present in an amount effective to reduce or prevent sunburn caused from visible light.

Also disclosed herein is a method of reducing or preventing sunburn caused from visible light and UV radiation in a subject, comprising topically applying to the subject a sunscreen composition comprising (a) inorganic UV filtering agents comprising zinc oxide and titanium dioxide; (b) antioxidants comprising vitamin E or derivatives thereof and vitamin C or derivatives thereof; and (c) at least one inorganic pigment comprising iron oxide, wherein the at least one inorganic pigment and the antioxidants are present in an amount effective to reduce or prevent sunburn caused from visible light.

Further disclosed herein are methods of increasing an SPF of a sunscreen composition that comprises at least one inorganic UV filtering agent, the method comprising adding to the sunscreen composition (a) antioxidants comprising vitamin E or derivatives thereof and vitamin C or derivatives thereof; and (b) at least one inorganic pigment comprising iron oxide, wherein the at least one inorganic pigment and the antioxidants are present in an amount effective to increase the SPF of the sunscreen composition, such as, for example, an amount effective to increase the SPF of the sunscreen composition by an SPF of at least about 3, when the sunscreen composition is tested under outdoor solar exposure conditions.

According to certain embodiments, the inorganic UV filtering agents are present in the sunscreen composition in a total amount ranging from about 10% to about 50% by weight based on a total weight of the sunscreen composition. In certain embodiments, the antioxidants are present in the sunscreen composition in a total amount ranging from about 0.1% to about 5% by weight relative to the total weight of the sunscreen composition, and in certain embodiments, the at least one inorganic pigment is present in the sunscreen composition in a total amount ranging from about 0.1% to about 10% by weight relative to the total weight of the sunscreen composition.

In various embodiments of the disclosure, the iron oxide is chosen from the group consisting of black iron oxide, brown iron oxide, red iron oxide, yellow iron oxide, and mixtures thereof.

In certain embodiments, the zinc oxide has a mean particle size ranging from about 10 nm to about 100 nm, and in certain embodiments, the titanium dioxide has a mean particle size ranging from about 5 nm to about 20 nm. In various aspects of the disclosure, at least one of the zinc oxide, the titanium dioxide, and/or the at least one inorganic pigment (e.g., iron oxide) further comprises a coating, such as, for example, triethoxycaprylylsilane.

In certain aspects of the disclosure, the vitamin E or derivatives thereof is chosen from the group consisting of tocopherol and tocopherol acetate, and in certain aspects, the vitamin C or derivatives thereof is chosen from the group consisting of ascorbic acid and tetrahexyldecyl ascorbate.

In certain embodiments, the sunscreen compositions disclosed herein further comprise at least one additional ingredient selected from the group consisting of emollients, organic UV filtering agents, skin conditioning agents, preservatives, and silica, and in certain embodiments, the sunscreen compositions disclosed herein do not comprise an organic UV filtering agent.

In certain embodiments, the at least one inorganic pigment further comprises at least one inorganic pigment selected from the group consisting of pigmentary zinc oxide and pigmentary titanium dioxides. For instance, in certain embodiments, the pigmentary zinc oxide may have a mean particle size ranging from greater than about 100 nm to about 1000 nm, and in certain embodiments, the pigmentary titanium dioxide may have a mean particle size ranging from 1 μm to about 20 μm.

It is to be understood that both the foregoing general description and the following detailed description are exemplary and explanatory only and are not restrictive of the present teachings, as claimed.

DESCRIPTION OF THE EMBODIMENTS

Reference will now be made in detail to embodiments of the present teachings. In the following description, reference is made to exemplary embodiments in which the present teachings may be practiced. The following description is, therefore, merely exemplary.

Disclosed herein is a sunscreen composition that provides protection to the skin against both the visible and UV portions of the sun's rays, as well as methods of using the sunscreen composition to reduce or prevent sunburn resulting from both the visible and UV portions of the sun's rays and methods of increasing the SPF of a sunscreen composition. The sunscreen compositions disclosed herein comprise pigments that absorb the sun's visible rays, primarily in the blue region, as well as antioxidants that help to quench free radicals induced by the sun's visible radiation, thereby reducing or preventing erythema.

In certain embodiments, disclosed herein is a sunscreen composition comprising at least one inorganic pigment such as iron oxide together with titanium dioxide and zinc oxide UV filtering agents, as well as a combination of antioxidants, such as vitamin E (tocopherol or derivatives thereof, such as tocopherol acetate) and vitamin C (ascorbic acid or derivatives thereof, such as tetrahexyldecyl ascorbate). The sunscreen compositions disclosed herein provide superior protection against erythema caused by sunlight as compared to conventional sunscreen products, including, for example, conventional sunscreens having an SPF of at least 60 (as determined, for example, using the protocol set forth by International Organization for Standardization (ISO) 24444: 2019). The at least one inorganic pigment such as iron oxide provides visible light protection together with the antioxidants vitamin E and vitamin C in a manner that is cosmetically-acceptable and can be adapted by concentration and color grades to match the skin tone of the user.

The sunscreen compositions disclosed herein may be formulated to provide a physical feel and touch characteristics to be pleasant to the user. In certain embodiments, the sunscreen compositions disclosed herein may further comprise, for example, at least one silicone-based emollient to provide a smooth and dry feel to the product after application. In certain embodiments, the sunscreen composition may further comprise silica.

DEFINITIONS

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. The following terms and cognates thereof shall have the following meanings unless the context clearly indicates otherwise.

The term "at least one of" is used to mean one or more of the listed items can be selected. For example, if the listing of items is A and B, at least one of A and B indicates A alone, B alone, or A and B.

The term "about" is understood as encompassing a range of normal variation as accepted in the art and can include, for example, within 10%, 1%, 0.1% or 0.01% of the stated value. Unless otherwise indicated, all numerical values provided herein are understood as being modified by the term about.

As used herein, the term "erythema" is used interchangeably with the term "sunburn" and indicates a superficial reddening of the skin caused by overexposure to waves from the electromagnetic spectrum, including both visible light and UV radiation. As used herein, erythema and sunburn are distinguished from increased skin pigmentation (e.g., tanning).

As used herein, the term "ultraviolet radiation" or "UV radiation" indicates electromagnetic radiation in the range of about 290 nm to about 400 nm. Within the spectrum of UV radiation, UVB radiation is electromagnetic radiation within the range of about 290 nm to about 320 nm, while UVA radiation is electromagnetic radiation within the range of about 320 to about 400 nm.

As used herein, the term "visible light" indicates electromagnetic radiation in the range of about 400 nm to about 700 nm. Within the visible light spectrum, the violet light region spans about 380-450 nm, the blue light region spans about 450-495 nm, the green light region spans about 495-570 nm, the yellow light region spans about 570-590 nm, the orange light region spans about 590-625 nm, and the red light region spans about 625-700 nm.

As used herein, the terms "sun protection factor" and "SPF" indicate a measure of how much solar energy is required to produce erythema, or sunburn, on skin after the application of a sunscreen composition relative to the amount of solar energy required to produce erythema on skin that does not have any sunscreen composition applied thereto. The amount of solar energy may be affected by both length (time) of exposure and intensity of the solar energy.

Solar intensity may be related to time of day, geographic location (wherein a higher latitude may increase solar intensity), and weather (e.g., cloud coverage).

As used herein, the term "effective amount" refers to an amount of a sunscreen composition which, when applied or administered in an appropriate quantity and frequency, is sufficient to prevent, reduce, or mitigate the damage incurred from sunburn.

Additional definitions are set forth throughout the detailed description.

Sunscreen Compositions

Disclosed herein are sunscreen compositions useful for reducing or preventing damage caused by visible light and UV radiation, including sunburn, when applied topically to a user's skin.

In certain embodiments there is disclosed a sunscreen composition comprising 1) inorganic UV filtering agents comprising or consisting of zinc oxide and titanium dioxide; (2) antioxidants comprising or consisting of vitamin E or derivatives thereof and vitamin C or derivatives thereof; and (3) at least one inorganic pigment comprising or consisting of iron oxide, wherein the at least one inorganic pigment and the antioxidants are present in an amount effective to reduce or prevent sunburn caused from visible light.

UV Filtering Agents

In certain embodiments, the sunscreen composition comprises at least one inorganic UV filtering agent selected from the group consisting of titanium dioxide, zinc oxide, cerium oxides, zirconium oxides, and mixtures thereof. Inorganic UV filtering agents may serve to filter, or absorb, UV radiation from the UV band of the electromagnetic spectrum, including, for example, UVA and UVB radiation at approximately 320-400 nm and 280-320 nm, respectively.

In various embodiments of the disclosure, the sunscreen composition comprises zinc oxide as an inorganic UV filtering agent. Zinc oxide may be present as a solid particle that is micronized or nanosized, for example having a mean particle size ranging from about 10 nm to about 400 μm, such as from about 10 nm to about 25 μm, from about 10 nm to about 10 μm, or from about 15 nm to about 5 μm. As used herein, "nanosized" or "nanoparticles" indicates a particle size that is under about 1000 nm, such as from about 1 nm to about 1000 nm or from about 1 nm to about 100 nm, while "micronized" or "microsized" indicates a particle size that ranges from about 1 μm (i.e., about 1000 nm) to about 1000 μm. In embodiments where zinc oxide is present as a UV filtering agent, the zinc oxide may comprise nanoparticles having a mean particle size ranging from about 5 nm to about 1000 nm, such as from about 10 nm to about 1000 nm, from about 30 nm to about 200 nm, from about 40 nm to about 100 nm, from about 60 nm to about 80 nm, from about 10 nm to 50 nm, or from about 25 nm to about 40 nm, or about 80 nm. As discussed below, however, zinc oxide may also be present in the sunscreen compositions disclosed herein as at least one inorganic pigment in pigmentary sizes, indicating that the zinc oxide may be larger than nanoparticle-sized, having a mean particle size ranging from about 100 nm to about 1000 nm, such as about 200 nm to about 500 nm, or from about 1 μm to about 400 μm, such as from about 10 μm to about 100 μm, from about 2 μm to about 25 μm, from about 5 μm to about 20 μm, or from about 10 μm to about 15 μm. In certain embodiments, the zinc oxide comprises a mixture of nanoparticles (e.g., for UV filtering protection) and particles of a larger, micronized size (e.g., for visible light scattering protection).

Zinc oxide may be present in the sunscreen composition in any amount effective to filter UV rays so as to prevent or reduce the effects of sunburn when applied topically to a user, either alone or together with other components of the sunscreen. In embodiments, zinc oxide may be present in the sunscreen composition in an amount ranging from about 1% to about 25%, such as from about 5% to about 20%, or from about 10% to about 15%, such as about 10%, about 11%, about 12%, about 13%, or about 15%, by weight based on the total weight of the sunscreen composition.

In certain embodiments, in addition to or instead of zinc oxide, the sunscreen compositions disclosed herein may comprise titanium dioxide as an inorganic UV filtering agent. As discussed above for zinc oxide, the titanium dioxide may be present as a solid particle that is micronized or nanosized, for example having a mean particle size ranging from about 10 nm to about 100 μm, such as from about 10 nm to about 25 μm, from about 10 nm to about 10 μm, or from about 15 nm to about 5 μm. In certain embodiments where titanium dioxide is present as a UV filtering agent, the titanium dioxide may comprise nanoparticles having a mean particle size ranging from about 5 nm to about 1000 nm, such as from about 5 nm to about 500 nm, from about 10 nm to 50 nm, or from about 15 nm to about 40 nm, or about 15 nm. Titanium dioxide nanoparticles may also form agglomerates having a larger mean particle size, such as, for example, a mean agglomerate particle size ranging from about 100 nm to about 1000 nm, such as, for example, about 200 nm to about 500 nm, or about 250 nm to about 400 nm. In certain embodiments, the titanium dioxide may be larger than nanoparticle-sized, having a mean particle size ranging from about 1 μm to about 25 μm, such as from about 5 μm to about 20 μm, or from about 10 μm to about 15 μm. In certain embodiments, the titanium dioxide comprises a mixture of nanoparticles (e.g., for UV filtering protection) and particles of a larger, micronized size (e.g., for visible light scattering protection).

Titanium dioxide may be present in the sunscreen composition in any amount effective to filter UV rays so as to prevent or reduce the effects of sunburn when applied topically to a user, either alone or together with other components of the sunscreen. In embodiments, titanium dioxide may be present in the sunscreen composition in an amount ranging from about 1% to about 25%, such as from about 5% to about 20%, or from about 5% to about 15%, such as about 5%, about 6%, about 7%, about 8%, about 9%, about 10%, about 11%, about 12%, about 13%, about 14%, or about 15%, by weight based on the total weight of the sunscreen composition.

In total, the inorganic UV filtering agents, including both zinc oxide and titanium dioxide, may be present in the sunscreen composition in an amount ranging from about 2% to about 50%, such as from about 5% to about 50%, from about 10% to about 45%, or from about 15% to about 20%, such as about 15%, about 16%, about 17%, about 18%, about 19%, about 20%, about 21%, about 22%, about 23%, about 24%, or about 25%, by weight based on the total weight of the sunscreen composition.

In certain embodiments, the at least one inorganic UV filtering agent may be a surface-treating inorganic UV filtering agent. Surface treating the at least one inorganic UV filtering agent may reduce or prevent photoreactivity of the agent and/or aid in mixing with other ingredients in the sunscreen composition. A surface-treated inorganic UV filtering agent indicates that the UV filtering agent has been surface-treated by any means, including chemical, electrical, and/or mechanical means. In certain embodiments, surface treating the at least one inorganic UV filtering agent may enhance the water-resistance properties of the UV filtering agent and the sunscreen composition. In certain embodiments, all of the UV filtering agents present in the sunscreen composition are surface-treated.

An inorganic UV filtering agent may be surface-treated by any surface-treating method or agent known in the art. In certain embodiments, the at least one inorganic UV filtering agent may comprise coated particles. The coating may comprise, for example, hydrophobic materials such as alkyl siloxanes (e.g., triethoxycaprylylsilane), organotitanates, halogenated phosphates (e.g., perfluoroalkyl phosphonates), halogenated organosilanes, modified amino acids (e.g., disodium stearoyl glutamate), silicones, or metal salts of fatty acids.

Exemplary embodiments of a surface-treated coated UV filtering agent may include, for example, coated zinc oxide, such as triethoxycaprylylsilane zinc oxide (e.g., Z-Cote® HP1), and/or coated titanium dioxide, such as triethoxycaprylylsilane titanium dioxide (e.g., CM3K40T4 by Kobo products, Inc. and UV Cut $TiO_2$-41).

Inorganic Pigments

In various embodiments, the sunscreen compositions disclosed herein may further comprise at least one inorganic pigment. While not wishing to be bound by theory, it is believed that the inorganic pigment acts to absorb the sun's visible rays, such as visible light in the blue light region of the visible light spectrum (e.g., about 450 nm to about 495 nm) and the violet light region of the visible light spectrum (e.g., about 380 nm to about 450 nm), which may overlap with UVA radiation at the upper end range of the UVA spectrum (e.g., about 375 nm to about 400 nm). Exemplary inorganic pigments may include titanium dioxide; zinc oxide; iron oxides, including black iron oxide, brown iron oxide, red iron oxide, and yellow iron oxide; manganese violet; ultramarine blue; chromium oxide, chromium hydrate; ferric blue; and mixtures thereof. In certain embodiments, the at least one inorganic pigment comprises a mixture of iron oxides, such as a mixture of red, yellow, and black iron oxides.

In one embodiment, the at least one inorganic pigment comprises iron oxide and at least one of zinc oxide and titanium dioxide, and in one embodiment, the at least one inorganic pigment comprises iron oxide and titanium dioxide. While traditional nanosized particles of inorganic UV filtering agents such as titanium dioxide and zinc oxide may serve to provide UVB protection against radiation in the range of from about 280 nm to about 320 nm, these agents often fail to provide adequate protection from erythema in the higher radiation wavelengths constituting UVA radiation, such as from about 315 nm to about 400 nm, including from about 375 nm to about 400 nm. As disclosed herein, however, the addition of at least one inorganic pigment such as iron oxide, titanium dioxide, and/or zinc oxide may provide enhanced protection against erythema from UVA radiation and/or visible light, including, for example protection from UVA radiation in the range of about 375 nm to about 400 nm and visible light in the range of from about 400 nm to about 750 nm.

In embodiments wherein the at least one inorganic pigment comprises titanium dioxide and/or zinc oxide, the titanium dioxide and/or zinc oxide may have a particle size that is larger than the titanium dioxide and/or zinc oxide that comprises the UV filtering agents. Smaller nanosized particles of titanium dioxide and/or zinc oxide are known to provide broad-spectrum UV filtering and absorbing properties, but have a reduced ability to scatter and reflect visible light, making them more transparent when applied to the skin in the form of a sunscreen composition. See, e.g., Yin, H. et al., *A comparative study of the physical and chemical properties of nano-sized ZnO particles from multiple batches of three commercial products*, J. Nanopart. Res. 2015; 17:1-19.

Accordingly, in certain embodiments wherein the sunscreen composition disclosed herein comprises UV filtering agents of nanoparticles of zinc oxide and/or nanoparticles of titanium dioxide, the sunscreen composition may further comprise at least one inorganic pigment selected from the group consisting of pigmentary-sized zinc oxide and pigmentary-sized titanium dioxide. By "pigmentary" or "pigmentary-sized," it is indicated that the mean particle size of the titanium dioxide and/or zinc oxide is larger than the aforementioned nanosized particles and is of a cosmetically-acceptable size for use as a pigment in the sunscreen composition. In certain embodiments, pigmentary-sized particles of zinc oxide may have a mean particle size ranging from at least about 100 nm to about 25 µm, such as from about 200 nm to about 10 µm, from about 200 nm to about 500 nm, or from about 5 µm to about 15 µm. In certain embodiments, pigmentary-sized particles of titanium dioxide may have a mean particle size ranging from at least about 100 nm to about 25 µm, such as from about 200 nm to about 10 µm, from about 200 nm to about 500 nm, from about 5 µm to about 15 µm, or from about 8 µm to about 10 µm.

The at least one inorganic pigment may be present in the sunscreen composition in any amount effective to absorb visible light, such as visible light from the blue and/or violet regions of the visible light spectrum, either alone or together with other components of the sunscreen composition. In certain embodiments, the at least one inorganic pigment is present in the sunscreen composition in an amount ranging from about 0.01% to about 10% by weight, such as from about 1% to about 5%, or from about 1% to about 4.5%, based on the total weight of the sunscreen composition.

In certain embodiments, the at least one inorganic pigment may be a surface-treated inorganic pigment. Surface treating the at least one inorganic pigment may reduce or prevent photoreactivity of the pigment and/or aid in mixing with other ingredients in the sunscreen composition. A surface-treated inorganic pigment indicates that the inorganic pigment has been surface-treated by any means, including chemical, electrical, and/or mechanical means. In certain embodiments, surface treating the at least one inorganic pigment may enhance the water-resistance properties of the inorganic pigment and the sunscreen composition. In certain embodiments, all of the inorganic pigments present in the sunscreen composition are surface-treated.

An inorganic pigment may be surface-treated by any surface-treating method or agent known in the art. In certain embodiments, the at least one inorganic pigment may comprise coated particles. The coating may comprise, for example, hydrophobic materials such as alkyl siloxanes (e.g., triethoxycaprylylsilane), organotitanates, halogenated phosphates (e.g., perfluoroalkyl phosphonates), halogenated organosilanes, modified amino acids (e.g., disodium stearoyl glutamate), silicones, or metal salts of fatty acids.

Exemplary embodiments of in organic pigments may include surface-treated coated inorganic pigments such as coated iron oxides, including triethoxycaprylylsilane iron oxides (e.g., Unipure®) and coated and uncoated titanium dioxides (e.g., Unipure® White LC 987 and Unipure® White LC 987 AS-EM, a triethoxycaprylylsilane titanium dioxide).

Antioxidants

In certain embodiments disclosed herein, the sunscreen composition further comprises at least one antioxidant.

While not wishing to be bound by theory, it is believed that the at least one antioxidant helps to quench free radicals induced by the sun's visible light radiation, thereby effectively preventing or reducing sunburn when applied topically to a user in an amount effective to quench free radicals. In certain embodiments, the at least one antioxidant may be selected from vitamin A, vitamin C, vitamin E, selenium, carotenoids (e.g., beta-carotene), thiols, and derivatives and mixtures thereof. In certain embodiments, the at least one antioxidant is vitamin E (e.g., tocopherol) or a derivative thereof, such as tocopherol acetate. In certain embodiments, the at least one antioxidant is vitamin C (e.g., ascorbic acid) or a derivative thereof, such as tetrahexyldecyl ascorbate. In certain aspects of the disclosure, the at least one antioxidant comprises both vitamin E or a derivative thereof and vitamin C or a derivative thereof.

The at least one antioxidant may be present in the sunscreen compositions disclosed herein in any amount effective to prevent or reduce sunburn caused from the visible light region of the electromagnetic spectrum (e.g., about 400-750 nm), either alone or together with other components of the sunscreen composition. In certain embodiments, vitamin C or a derivative thereof, such as tetrahexyldecyl ascorbate, is present in the sunscreen composition in an amount ranging from about 0.01% to about 5%, such as from about 0.1% to about 3%, from about 0.2% to about 2%, or from about 0.2% to about 1%, by weight relative to the total weight of the sunscreen composition. In certain embodiments, vitamin E or a derivative thereof, such as tocopherol acetate, is present in the in the sunscreen composition in an amount ranging from about 0.01% to about 5%, such as from about 0.1% to about 3%, from about 0.2% to about 2%, or from about 0.2% to about 1%, by weight relative to the total weight of the sunscreen composition. In certain embodiments, the at least one antioxidant is a combination of vitamin C or a derivative thereof and vitamin E or a derivative thereof, and is present in the sunscreen composition in an amount ranging from about 0.1% to about 10%, such as from about 0.2% to about 5%, from about 0.5% to about 4%, or from about 0.4% to about 2%, by weight relative to the total weight of the sunscreen composition.

Additional Ingredients

The sunscreen compositions of the present disclosure may comprise any other additional ingredients known in the art to be cosmetically acceptable for use in a topical sunscreen product. For example, in certain embodiments, the sunscreen compositions disclosed herein may further comprise at least one of emollients/oils, emulsifiers, SPF boosters, organic pigments, organic UV filtering agents, skin conditioning agents, film formers, fillers, preservatives, fragrances, silica, sodium chloride, citric acid, neutralizing or pH-adjusting agents (e.g., triethanolamine and sodium hydroxide), essential oils, and cosmetically-acceptable carriers, including water.

In certain embodiments, the sunscreen composition further comprises at least one organic UV filtering agent, and in certain embodiments, the sunscreen composition does not comprise an organic UV filtering agent, such that the only UV filtering agents in the sunscreen composition are inorganic UV filtering agents. Traditional organic UV filtering agents are small, aromatic molecules, although any organic UV filtering agent known in the art may be considered within the scope of embodiments disclosed herein. For example, the at least one organic UV filtering agent disclosed herein may be selected from benzophenones (such as benzophenone-3, benzophenone-5, and benzophenone-8), 3-benzylidene camphor, bis ethylhexyloxyphenol methoxyphenyl triazine, butylmethoxy dibenzoyl methane, camphor benzalkonium methosulfate, diethylamino hydroxybenzoyl hexyl benzoate, diethylhexyl butamido triazone, drometrizole trisiloxane, ethoxyethyl methoxycinnamate, ethylhexyl dimethylamino benzoate, ethylhexyl methoxycinnamate, ethylhexyl salicylate, ethylhexyl triazone, homosalate, isoamyl p-methoxycinnamate, methyl anthranilate, 4-methylbenzylidene camphor, methylene bis-benzotriazolyl tetramethylbutylphenol, octocrylene, para aminobenzoic acid (PABA), polyacrylamide methylbenzylidene camphor, polysilicone-15, triethanolamine salicylate, and terephtalydene dicamphor sulfonic acid.

In certain embodiments, the sunscreen composition further comprises at least one humectant, such as, for example, butylene glycol or glycerin.

In certain embodiments, the sunscreen composition may comprise at least one emollient. Suitable emollients may be chosen from any emollient known in the art, including, for example, mineral oils, petroleum, vegetable/plant oils such as triglycerides (e.g., caprylic/capric triglycerides), waxes (e.g., beeswax), isopropyl palmitate, isopropyl myristate, diisopropyl adipate, dibutyl adipate, butyloctyl salicylate, C12-C15 alkyl benzoates, silicone oils (e.g., dimethicone and stearyl dimethicone), animal oils, hydrocarbon oils, and fatty acids. By way of example, the at least one emollient may be chosen from alkane oils such as isododecane and isohexadecane, ester oils, ether oils (e.g., dicaprylyl ether), and artificial triglycerides (e.g., capryl caprylyl glycerides, glyceryl trimyristate, glyceryl tripalmitate, glyceryl trilinolenate, glyceryl trilaurate, glyceryl tricaprate, glyceryl tricaprylate, glyceryl tri (caprate/caprylate), glyceryl tri (caprate/caprylate/linolenate, and mixtures thereof).

Exemplary ester oils may include, for example, ethyl palmitate; ethylhexyl palmitate; isopropyl palmitate; dicaprylyl carbonate; alkyl myristates such as isopropyl myristate and ethyl myristate; isocetyl stearate; 2-ethylhexyl isononanoate; isononyl isononanoate; isodecyl neopentanoate; isostearyl neopentanoate; diethyl sebacate; isopropyl lauroyl sarcosinate; diisopropyl sebacate; bis (2-ethylhexyl) sebacate; diisopropyl adipate; di-n-propyl adipate; dioctyl adipate; bis (2-ethylhexyl) adipate; diisostearyl adipate; bis (2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate; diisopropyl adipate; dioctyl adipate; 2-ethylhexyl hexanoate; ethyl laurate; cetyl octanoate; octyldodecyl octanoate; myristyl propionate; 2-ethylhexyl 2-ethylhexanoate; 2-ethylhexyl octanoate; 2-ethylhexyl caprylate/caprate; methyl palmitate; isononyl isononanoate; isohexyl laurate; hexyl laurate; isopropyl isostearate; isodecyl oleate; glyceryl tri (2-ethylhexanoate); pentaerythrithyl tetra (2-ethylhexanoate); 2-ethylhexyl succinate; C10-30 cholesterol/lanosterol esters; and mixtures thereof.

In certain embodiments, the sunscreen composition may further comprise at least one SPF booster. An SPF booster is a compound that acts to refract UV radiation, thereby increasing the UV absorption abilities of another compound, such as a UV filtering agent, when both compounds are together. The SPF booster may increase the path length of the UV radiation as it passes through the sunscreen composition. The at least one SPF booster may be chosen from any SPF boosters known in the art, including, for example, diethylhexyl syringylidenemalonate; glass microspheres such as calcium aluminum borosilicate, sodium borosilicate, and calcium/sodium borosilicate; and copolymers of styrene and (meth)acrylic acid.

In certain embodiments, the sunscreen composition may further comprise at least one preservative. Suitable preservatives may include, but are not limited to, chlorophenesin, sorbic acid, disodium ethylenedinitrilotetraacetate, ethylhexylglycerin, phenoxyethanol, methylparaben, ethylparaben, propylparaben, phytic acid, imidazolidinyl urea, sodium dehydroacetate, benzyl alcohol, sodium benzoate, methylchloroisothiazolinone, methylisothiazolinone, and mixtures thereof.

In certain embodiments, the sunscreen composition may further comprise at least one skin-conditioning agent, which, in certain embodiments, may also function as a film former and/or emulsifier. Suitable skin conditioning agents may include, but are not limited to, glycerins, such as ethoxylated glycerine and propoxylated glycerine; sugar alcohols such as propylene glycol, dipropylene glycol, butylene glycol, hexylene glycol, pentylene glycol, polypropylene glycol, polyethylene glycol, caprylyl glycol, sorbitol, hydroxypropyl sorbitol, erythritol, threitol, pentaerythritol, xylitol, glucitol, and mannitol; hexane triol (e.g., 1,2,6-hexanetriol); glyceryl stearate; dimethicone; cyclomethicone; phenyl trimethicone; phenyl dimethicone; cetyl dimethicone; stearyl dimethicone; caprylyl methicone; amodimethicone; C30-45 alkyl dimethicones and methicones; cetearyl methicone; dimethicone copolyol; cyclopentasiloxane (such as Bentone Gel®); dimethicone crosspolymers; dimethicone/vinyl dimethicone crosspolymers; C30-45 alkyl cetearyl dimethicone crosspolymers; cetearyl dimethicone crosspolymers; dimethicone/phenyl vinyl dimethicone crosspolymer; vinyl dimethicone/lauryl dimethicone crosspolymer; trifluoropropyl dimethicone/trifluoropropyl divinyldimethicone crosspolymer; trimethylsiloxysilicate; trisiloxane; neopentyl glycol diheptanoate; neopentyl glycol diethylhexanoate; neopentyl glycol dicaprylate/dicaprate; neopentyl glycol diglycidyl ether; neopentyl glycol dicaprate; neopentyl glycol diisostearate; butyloctyl salicylate; ethylhexyl stearate; diethylhexyl 2,6-naphthalate; petrolatum; beeswax; shea butter; shea butter oil; cocoa butter; jojoba butter; aloe butter; olive butter; coconut oil; jojoba oil; olive oil; sunflower seed oil; and mixtures thereof.

In certain embodiments, the sunscreen composition may further comprise at least one film former. Suitable film formers may include, but are not limited to, polyurethanes, acrylates/dimethicone crosspolymer, waxes, silicone acrylates, and mixtures thereof.

The sunscreen compositions disclosed herein may be prepared by any means known in the art, such as mixing and blending the ingredients of the composition in any manner acceptable in the art. In certain embodiments, the sunscreen composition may be prepared by combining ingredients into a commercially-available topical carrier, which may comprises other ingredients dissolved or dispersed therein, such as film formers, surfactants, emulsifiers, thickeners, emollients, preservatives, pH adjusters, colorants, and fragrances, for example.

Methods of Using Sunscreen Compositions

Also disclosed herein are methods of reducing or preventing sunburn. The methods disclosed herein may comprise topically applying an effective amount of a sunscreen composition as disclosed herein to a surface of the user's body, such as, for example, the hair, skin, nails, or lips. As used herein, an effective amount can be any amount that reduces or prevents sunburn from exposure to both UV radiation and visible light. In certain embodiments, an effective amount may range, for example, from about 0.5 mg/cm$^2$ to about 5 mg/cm$^2$, such as from about 1 mg/cm$^2$ to about 3 mg/cm$^2$, or about 2 mg/cm$^2$. In certain embodiments, the methods disclosed herein further comprise allowing the sunscreen composition to dry after application. In certain embodiments, the sunscreen may be allowed to dry for a time period ranging from about 5 minutes to about 30 minutes, such as about 10 minutes, about 15 minutes, about 20 minutes, or about 25 minutes.

By topically applying the sunscreen composition, it is understood to mean that the sunscreen composition may be applied to any surface of the user, including, for example, the skin, hair, nails, and/or lips. The sunscreen composition may be topically applied in any manner known in the art, including by spray application, wiping, laying, spreading, or rubbing with hands or with an applicator, such as a spray bottle, wipe, roller, etc.

Also disclosed herein are methods of increasing the SPF of a sunscreen composition, the method comprising adding at least one inorganic pigment and at least one antioxidant to a sunscreen composition. SPF, or sun protection factor, may be measured by any means known in the art and as described herein. In one embodiment, SPF may be measured by the protocol set forth by the International Organization for Standardization (ISO) 24444:2019, which measure SPF in an indoor laboratory in terms of the ratio of [the amount of UV radiation required to produce erythema on sunscreen-protected skin] to [the amount of UV radiation required to produce erythema on sunscreen-unprotected skin]. As the standard set forth in ISO 24444:2019 defines SPF in terms of UV radiation (i.e., under 400 nm), it does not consider, and in fact excludes, the effects of real-life solar exposure, including the effects of visible light. Indeed, laboratory-based SPF testing typically uses solar stimulators that emit UV radiation only in the 290-400 nm region of the spectrum, while adding filters to eliminate radiation below 290 nm and above 400 nm, and significantly diminish the content between 380 and 400 nm. Accordingly, the effects of long wavelength UVA and visible light on skin are not taken into account in many SPF determinations, including indoor labo-ratory-based SPF determinations that are used for many commercially-available sunscreen products.

In various aspects of the methods disclosed herein, SPF is determined based on actual outdoor solar exposure and may be defined in terms of the ratio of [the least amount of solar exposure required to produce erythema on sunscreen-pro-tected skin] to [the amount of solar exposure required to produce erythema on sunscreen-unprotected skin]. Thus, SPF as used herein accounts for all of the effects from actual outdoor solar exposure, including both UV radiation and visible light and represent the performance of the product under actual use conditions.

In various aspects of the disclosure, the SPF of the sunscreens disclosed herein may be increased by an SPF of at least about 3, such as at least about 4, at least about 5, or at least about 6, as compared to a sunscreen composition that does not contain an effective amount of at least one anti-oxidant and/or an effective amount of at least one inorganic pigment, when tested under outdoor solar exposure condi-tions. In certain aspects, the SPF of the sunscreens disclosed herein may be increased by an SPF ranging from about 2 to about 10, such as from about 3 to about 5, or from about 3 to about 4, when tested under outdoor solar exposure con-ditions. While this level of increase may appear small relative to SPF claims generated with indoor solar simulator test methods, it is in fact proportionally much higher in impact when comparing products tested in outdoor condi-tions, where the maximum observed SPF values for SPF 60-100 claiming sunscreens is in the 8 to 10 range. Thus an increase of 2-6 SPF units above this 8 to 10 maximal observed results in outdoor use conditions represent a sig-nificant boost in real protection.

Notwithstanding that the numerical ranges and param-eters setting forth the broad scope of the disclosure are approximations, the numerical values set forth in the specific examples are reported as precisely as possible. Any numeri-cal value, however, inherently contains certain errors nec-essarily resulting from the standard deviation found in their respective testing measurements. Moreover, all ranges dis-closed herein are to be understood to encompass any and all sub-ranges subsumed therein.

While the present teachings have been illustrated with respect to one or more implementations, alterations and/or modifications can be made to the illustrated examples with-out departing from the spirit and scope of the appended claims. In addition, while a particular feature of the present teachings may have been disclosed with respect to only one of several implementations, such feature may be combined with one or more other features of the other implementations as may be desired and advantageous for any given or particular function. Furthermore, to the extent that the terms "including," "includes," "having," "has," "with" or variants thereof are used in either the detailed description and the claims, such terms are intended to be inclusive in a manner similar to the term "comprising." Further, in the discussion and claims herein, the term "about" indicates that the value listed may be somewhat altered, as long as the alteration does not result in nonconformance of the process or struc-ture to the illustrated embodiment. Finally, "exemplary" indicates the description is used as an example, rather than implying that it is an ideal.

It will be appreciated that variants of the above-disclosed and other features and functions, or alternatives thereof, may be combined into many other different systems or applica-tions. Various presently unforeseen or unanticipated alter-natives, modifications, variations, or improvements therein may be subsequently made by those skilled in the art which are also intended to be encompasses by the following claims.

EXAMPLES

Example 1

Sunscreen compositions were formulated as shown below in Table 1.

TABLE 1

| | | | |
|---|---|---|---|
| Sunscreen formulations for GM1, GM2, and GM3 | | | |
| Ingredient | GM1 (iron oxide + antioxidants) (% by weight) | GM2 (comparative without iron oxide or antioxidants) (% by weight) | GM3 (comparative with antioxidants, without iron oxide) (% by weight) |
| Neopentyl glycol diheptanoate | 6.390 | 10.280 | 9.280 |
| Isohexadecane | 10.000 | 12.010 | 11.010 |

TABLE 1-continued

| Ingredient | GM1 (iron oxide + antioxidants) (% by weight) | GM2 (comparative without iron oxide or antioxidants) (% by weight) | GM3 (comparative with antioxidants, without iron oxide) (% by weight) |
|---|---|---|---|
| Titanium dioxide, as CM3K40T4 (33% TiO₂); mean particle size 15 nm; aggregate particle size 120 nm | 35.380 | 35.380 | 35.380 |
| Zinc oxide, as Z-Cote ® HP1, mean particle size 80 nm | 11.000 | 11.000 | 11.000 |
| Iron oxides (yellow, black, and red), triethoxycaprylylsilane | 4.500 | 0.000 | 0.000 |
| Silica | 1.500 | 2.000 | 2.000 |
| Beeswax | 4.500 | 4.500 | 4.500 |
| Stearyl dimethicone, octadecene | 5.000 | 5.000 | 5.000 |
| C10-30 cholesterol/lanosterol esters | 0.500 | 0.500 | 0.500 |
| Cyclopentasiloxane, acrylates/dimethicone crosspolymer, and trimethylsiloxysilicate | 5.000 | 5.000 | 5.000 |
| Preservative | 0.500 | 0.500 | 0.500 |
| Tetrahexyldecyl ascorbate | 1.000 | 0.000 | 1.000 |
| Tocopherol acetate | 1.000 | 0.000 | 1.000 |
| Cyclopentasiloxane, stearalkonium hectorite, propylene carbonate | 12.000 | 12.000 | 12.000 |
| Silica cetyl silylate | 1.500 | 1.600 | 1.600 |
| Fragrance | 0.230 | 0.230 | 0.230 |
| TOTAL | 100.000 | 100.000 | 100.000 |

Table 1 provides formulations for a sunscreen according to the present disclosure (GM1) and two comparative formulations (GM2 and GM3) that were compounded for clinical testing in Arequipa, Peru, in late November, between 10:00 am and 12:30 pm local time (solar noon 11:00 am). The GM2 "placebo" formulation contains the ingredients for a conventional sunscreen product with 10% micronized titanium dioxide and 11% micronized zinc oxide, but without the antioxidants vitamin E or vitamin C or the inorganic pigment iron oxide. GM3 is also a conventional sunscreen that further comprises antioxidants in the formulation in an amount of 1% by weight each, but does not contain iron oxide. The GM1 formulation adds both the antioxidants as well as iron oxides (yellow, black, and red iron oxide) in ratios to match a skin's color. While the percentages of the titanium dioxide and zinc oxide very slightly by formula because of the addition of the iron oxides and antioxidant additives, the actual amount of titanium dioxide and zinc oxide in each batch was the same after adjusting the concentration of the emollient.

The three formulations and an ISO reference standard SPF 63 formulation (containing no visible light protection, including no iron oxide or antioxidants) were tested on 11 subjects for SPF value in outdoor, natural sunlight exposures in Arequipa, Peru, at around 7,500 feet elevation, near solar solstice around solar noon. The sunburning UV intensity ranged from 7.5 to 8 sunburn doses per hour during this period (i.e., roughly 7.5-8 minutes exposure needed to get a sunburn). This is a more intense UV environment as compared to typical exposure times of 15-20 minutes for a sunburn in North America or Europe. The high sun angle (87° zenith) combined with the higher elevation yielded maximal UV content relative to the visible light content.

The three sunscreen formulations above were applied to rectangular areas on the backs of the test subjects at a density of 2 mg/cm² as designated by recognized SPF testing protocols. The products were covered and allowed to dry for at least 15 minutes. Test areas were outlined by aluminum foil tape and were exposed to sunlight for varying amounts of UV exposure as measured by a sunburning UV dosimeter. As pre-determined dose exposures were reached, the associated test site was covered with aluminum foil tape to end the exposure to that site. Exposures were also conducted on non-sunscreen areas to determine the unprotected minimal dose of radiation causing a sunburn. At the end of all of the exposures, the exposed back areas of the subjects were covered, and the subjects were instructed to stay out of the sun and keep their backs completely covered for the remainder of the day.

The following morning (about 16-24 hours post exposure), the subjects exposure sites were examined, and the lowest dose of exposure causing a sunburn reaction, called the minimal erythema dose ("MED"), was determined for both the sunscreen protected sites, as well as the unprotected site. The ratio of doses (sunscreen protected dose/unprotected dose) was calculated as the SPF value of the test product (as is done in conventional laboratory SPF testing). The protection values were then compared for each of the four test products GM1, GM2, GM3, and the SPF 63 Reference product. The calculated SPF for each of the sunscreen formulations test is shown below in Table 2.

TABLE 2

| Natural sunlight SPF values for GM1-GM3 and SPF 63 Reference | | | |
|---|---|---|---|
| GM1 | GM2 | GM3 | SPF 63 Reference |
| 11.9 | 8.1 | 8.8 | 8.5 |

These data demonstrate that a formulation containing the addition of antioxidants (GM3) provides additional protection for the SPF as compared to a formulation without antioxidants (GM2) (i.e., 8.8 versus 8.1), having a p-value of p<0.08. Adding the iron oxides to the formulation along with the antioxidants (GM1) made a significant difference, increasing the SPF value to 11.9, as compared to GM2's 8.1 (p<0.001). The SPF 63 ISO reference standard with no visible light protection only showed an SPF of 8.5 instead of the expected SPF of 63 as tested in clinical SPF testing laboratories. The difference between these two results may be due to the fact that the solar simulator used in clinical SPF testing does not contain any visible light—it is (by design) removed from the spectral output of the simulator in order to reduce the potential heat burden to the skin during testing. Thus, the difference between the SPF 63 obtained in clinical SPF testing and the 8.5 value determined in natural sunlight with optimal UV content, is largely attributable to the presence of visible light in the testing source. The inventive sunscreen GM1 is surprisingly far superior to the SPF 63 reference standard sunscreen (p<0.003) when tested outdoors in real sunlight with the real solar spectrum, including visible light. This is due to GM1 providing the missing protection in the visible portion of the spectrum with the iron oxides and antioxidants.

If only 10% of the erythema damage of sunlight were caused by visible light, this would sufficient to reduce the protection of a SPF 63 sunscreen (1.6% transmission) to 8.6 (11.6% transmission), explaining the failure of this sunscreen in real sunlight testing. Similar findings of failure of high SPF products when tested in natural sunlight have been reported in the art. See, e.g., Lott, D., *Testing SPF* 15-100, *Indoor v. Outdoor*, COSMET. & TOIL. 2013; 128 (9): 638-647 and Hughes, S. N. G. et al., *Assessment of Natural Sunlight Protection Provided by* 10 *High SPF Broad Spectrum Sunscreens and Sun Protective Fabrics*, CURR. PROBL. DERMATOL. 2021; 55 (in press).

Example 2

An additional sunscreen formulation was prepared comprising tocopherol instead of tocopherol acetate, in combination with the Vitamin C derivative tetrahexyldecyl ascorbate, iron oxides, titanium dioxide, and zinc oxide for UV protection. The formulation is shown in Table 3 below.

TABLE 3

| Tinted sunscreen moisturizer | |
|---|---|
| Ingredient | Concentration (w/w %) |
| Butyloctyl salicylate | 7.5 |
| C12-C15 alkyl benzoate | 3.5 |
| Cyclopentasiloxane | 0.614 |
| Dimethicone | 1.5 |
| C10-C30 cholesterol/lanosterol esters | 0.3 |
| Phenoxyethanol, ethylhexylglycerin | 1.0 |
| Tetrahexyldecyl ascorbate | 0.2 |

TABLE 3-continued

| Tinted sunscreen moisturizer | |
|---|---|
| Ingredient | Concentration (w/w %) |
| Tocopherol | 0.2 |
| Lauryl PEG-9 polydimethylsiloxyethyl dimethicone | 1.0 |
| Cyclopentasiloxane, acrylates/dimethicone crosspolymer | 2.5 |
| Titanium Dioxide, as UV Cut $TiO_2$-41 (31% $TiO_2$); mean particle size 274 nm | 25.806 |
| Zinc Oxide, as Z-Cote ® HP1; mean particle size 80 nm | 11.0 |
| Iron oxides (yellow, black, and red), triethoxycaprylylsilane | 0.97 |
| Dimethicone | 3.0 |
| Water, Preservatives | QS |
| Sodium chloride | 1.0 |
| Sodium Benzoate | 0.35 |
| Citric acid (50%) | 0.06 |
| TOTAL | 100.00 |

The formulation resulted in a beige lotion that provided excellent protection against sunburn and a pleasant color and feel upon application to the skin. The lotion was evaluated to determine its Critical Wavelength by in vitro UVA broad spectrum testing according to the protocol set forth in FDA Final Rule Docket No. FDA-1978-N-0018, entitled "Labeling and Effectiveness testing; Sunscreen Drug Products for Over-the-Counter Human Use." The critical wavelength was determined using an LS1000-6S-009 Labsphere Ultraviolet Transmittance Analyzer (Spectrometer); a Solar Light PMA 2101 Erythema Weighted Detector; and HD6 PMMA plates.

Five readings of three plates were performed. The critical wavelengths of the 3 tested samples was 374.20, 373.20, and 373.00 (mean 373.47 nm). The average UVA/UV ratio was 0.64, and the average UVA/UVB ratio was 0.49. The results are shown below in Table 4.

TABLE 4

| Critical Wavelength Testing of 3 Samples of Formulation | | | | |
|---|---|---|---|---|
| | SPF | T (UVA) | T (UVB) | Lambda Critical |
| # of sets | 3 | 3 | 3 | 3 |
| Mean | 48.52 | 15.56% | 1.18% | 373.47 |
| STD | 11.03 | 1.33% | 0.43% | 0.64 |
| COV | 22.74% | 8.57% | 36.60% | 0.17% |

What is claimed is:

1. A method of reducing or preventing sunburn caused from visible light and ultraviolet (UV) radiation in a subject, comprising topically applying to the subject a sunscreen composition comprising:

(a) inorganic UV filtering agents comprising nanosized zinc oxide and nanosized titanium dioxide, present in the sunscreen composition in a total amount ranging from about 10% to about 50% by weight based on a total weight of the sunscreen composition, wherein the nanosized zinc oxide has a mean particle size ranging from about 10 nm to about 100 nm and the nanosized titanium oxide has a mean particle size ranging from about 5 nm to about 500 nm;

(b) at least one antioxidant present in the sunscreen composition in a total amount ranging from about 0.1% to about 5% by weight relative to the total weight of the sunscreen composition; and (c) at least one inorganic pigment comprising iron oxide, present in the sunscreen composition in a total amount ranging from about 0.01% to about 5% by weight relative to the total weight of the sunscreen composition, wherein the at least one inorganic pigment and the at least one antioxidant are present in an amount effective to reduce or prevent sunburn caused from visible light.

2. The method according to claim 1, wherein the iron oxide is chosen from the group consisting of black iron oxide, brown iron oxide, red iron oxide, yellow iron oxide, and mixtures thereof.

3. The method according to claim 1, wherein the nanosized zinc oxide has a mean particle size ranging from about 60 nm to about 80 nm.

4. The method according to claim 1, wherein the nanosized titanium dioxide has a mean particle size ranging from about 5 nm to about 20 nm.

5. The method according to claim 1, wherein at least one of the nanosized zinc oxide, the nanosized titanium dioxide, and the iron oxide further comprises a coating.

6. The method according to claim 5, wherein the coating is triethoxycaprylylsilane.

7. The method according to claim 1, wherein at least one antioxidant is selected from vitamin A, vitamin C, vitamin E, selenium, carotenoids, thiols, and derivatives and mixtures thereof.

8. The method according to claim 7, wherein the vitamin E or derivatives thereof is chosen from the group consisting of tocopherol and tocopherol acetate or wherein the vitamin C or derivatives thereof is chosen from the group consisting of ascorbic acid and tetrahexyldecyl ascorbate.

9. The method according to claim 1, wherein the at least one inorganic pigment further comprises at least one inorganic pigment selected from the group consisting of a pigmentary zinc oxides and a pigmentary titanium dioxide.

10. The method according to claim 9, wherein the pigmentary titanium dioxide has a mean particle size ranging from about 1 μm to about 20 μm.

11. A method of increasing a sunscreen protection factor (SPF) of a sunscreen composition that comprises inorganic UV filtering agents comprising nanosized zinc oxide and nanosized titanium dioxide, wherein the nanosized zinc oxide has a mean particle size ranging from about 10 nm to about 100 nm and the nanosized titanium oxide has a mean particle size ranging from about 5 nm to about 500 nm, the method comprising adding to the sunscreen composition (a) at least one antioxidant present in the sunscreen composition in a total amount ranging from about 0.1% to about 5% by weight relative to the total weight of the sunscreen composition; and (b) at least one inorganic pigment comprising iron oxide present in the sunscreen composition in a total amount ranging from about 0.01% to about 5% by weight relative to the total weight of the sunscreen composition, wherein the inorganic pigments and at least one antioxidant are present in an amount effective to increase the SPF of the sunscreen composition when tested under outdoor solar exposure.

12. The method according to claim 11, wherein the SPF is increased by an SPF of at least about 3.

13. The method according to claim 11, wherein the sunscreen composition does not comprise an organic UV filtering agent.

14. The method according to claim 11, wherein the at least one inorganic pigment further comprises at least one inorganic pigment selected from the group consisting of pigmentary titanium dioxides and pigmentary zinc oxides.

15. The method according to claim 11, wherein the nanosized zinc oxide has a mean particle size ranging from about 60 nm to about 80 nm.

16. The method according to claim 11, wherein the nanosized titanium dioxide has a mean particle size ranging from about 5 nm to about 20 nm.

17. The method according to claim 11, wherein the at least one antioxidant is selected from vitamin A, vitamin C, vitamin E, selenium, carotenoids, thiols, and derivatives and mixtures thereof.

18. The method according to claim 17, wherein the vitamin E or derivatives thereof is chosen from the group consisting of tocopherol and tocopherol acetate or wherein the vitamin C or derivatives thereof is chosen from the group consisting of ascorbic acid and tetrahexyldecyl ascorbate.

19. The method according to claim 14, wherein the pigmentary titanium dioxide has a mean particle size ranging from about 1 μm to about 20 μm.

20. A sunscreen composition comprising:
(a) inorganic UV filtering agent comprising nanosized zinc oxide and nanosized titanium dioxide, present in the sunscreen composition in a total amount ranging from about 10% to about 50% by weight based on a total weight of the sunscreen composition, wherein the nanosized zinc oxide has a mean particle size ranging from about 10 nm to about 100 nm and the nanosized titanium oxide has a mean particle size ranging from about 5 nm to about 500 nm;
(b) at least one antioxidant present in the sunscreen composition in a total amount ranging from about 0.1% to about 5% by weight relative to the total weight of the sunscreen composition; and
(c) inorganic pigments comprising iron oxide present in the sunscreen composition in a total amount ranging from about 0.01% to about 5% by weight relative to the total weight of the sunscreen composition,
wherein the inorganic pigments and antioxidants are present in an amount effective to reduce or prevent sunburn caused from visible light.

* * * * *